US00PP24669P2

(12) United States Plant Patent
Smith

(10) Patent No.: US PP24,669 P2
(45) Date of Patent: Jul. 22, 2014

(54) ***CHRYSANTHEMUM* PLANT NAMED 'CIFZ0009'**

(50) Latin Name: *Chrysanthemum×morifolium*
Varietal Denomination: CIFZ0009

(71) Applicant: Syngenta Crop Protection AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 38 days.

(21) Appl. No.: 13/694,374

(22) Filed: Nov. 27, 2012

(51) Int. Cl.
*A01H 5/00* (2006.01)

(52) U.S. Cl.
USPC ..... Plt./289

(58) Field of Classification Search
USPC ..... Plt./289
See application file for complete search history.

*Primary Examiner* — Kent L Bell
(74) *Attorney, Agent, or Firm* — Joshua L. Price

(57) ABSTRACT

A new *Chrysanthemum* plant named 'CIFZ0009' particularly distinguished by the medium sized yellow colored inflorescences, medium sized rounded and mounded plant habit, and a natural season flowering response of mid-October.

1 Drawing Sheet

Latin name of the genus and species of the plant claimed: *Chrysanthemum×morifolium.*

Varietal denomination: 'CIFZ0009'.

BACKGROUND OF THE NEW PLANT

The present invention comprises a new *Chrysanthemum*, botanically known as *Chrysanthemum×morifolium,* and hereinafter referred to by the variety name 'CIFZ0009'.

'CIFZ0009' is a product of a planned breeding program. The new cultivar has medium sized yellow colored inflorescences, medium sized rounded and mounded plant habit, and a natural season response of mid-October.

'CIFZ0009' originated from a hybridization made in December 2007 in a greenhouse in Amanecer, Columbia. The female parent was the proprietary plant designated 'Yoelena', U.S. Plant Pat. No. 20,212, with larger sized inflorescences, larger overall plant size and a natural season flowering response that is up to 5 weeks slower and a blackcloth flowering response that is about 1 week slower when compared to 'CIFZ0009'.

The male parent of 'CIFZ0009' was the proprietary plant designated as 'Yodiana', U.S. Plant Pat. No. 17,535 with a bit lighter ray floret color, more disks florets, a natural season response that is up to 5 weeks faster and a blackcloth response that is about 1 week faster when compared to 'CIFZ0009'. The resultant seed was sown and grown outdoors in June 2009 in Alva, Fla. USA.

'CIFZ0009' was selected as one flowering plant within the progeny of the stated cross in November 2009 in Alva, Fla.

The first act of asexual reproduction of 'CIFZ0009' was accomplished when vegetative cuttings were propagated from the initial selection in January 2010 in a greenhouse in Alva, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIFZ0009' are firmly fixed and are retained through successive generations of asexual reproduction.

'CIFZ0009' has not been observed under all possible environmental conditions. The phenotype may vary significantly with variations in environment such as temperature, light intensity, and day length.

A Plant Breeder's Right for this cultivar was applied for in Canada on Feb. 24, 2012 (12-7528). 'CIFZ0009' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0009' with colors being as true as possible with an illustration of this type. The photographic drawing shows a flowering plant of the new variety and a close-up of an inflorescence.

DETAILED BOTANICAL DESCRIPTION

The plant descriptions and measurements were taken in Gilroy, Calif. in mid-August 2012 under natural light. These plants were grown one plant to a one gallon container and were about 12-14 weeks of age.

The aforementioned photographs were taken in late October 2011 outdoors in Monroeville, N.J. These plants were grown 1 plant to a 9 inch container with no terminal pinching. These plants were approximately 18 weeks of age. Color references are made to The Royal Horticultural Society Colour Chart (R.H.S.) 2001.

TABLE 1

DIFFERENCES BETWEEN THE NEW VARIETY 'CIFZ0009' AND A MOST SIMILAR VARIETY

| | 'CIFZ0009' | 'Golden Yoandrea' (U.S. Plant Pat. No. 16,384) |
|---|---|---|
| Inflorescence size: | Little smaller | Little larger |
| Inflorescence color: | Mono-tone | Two-toned |
| Plant habit: | Bit more compact and fuller | Bit less compact and not as full |
| Blackcloth response: | About 1 week slower | About 1 week faster |
| Natural season response: | About 1 week slower | About 1 week faster |

Plant:

*Form, growth and habit.*—Herbaceous garden-type, stems upright and outwardly spreading, freely branching, strong and moderately vigorous growth habit.

*Plant height.*—20-21.0 cm.

*Plant height (inflorescence included).*—24-26.0 cm.

*Plant width.*—About 40.0 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature, leaf color, upper surface.*—RHS 147A.

*Immature, leaf color, lower surface.*—RHS 137B.

*Mature, leaf color, upper surface.*—RHS 147A.

*Mature, leaf color, lower surface.*—RHS 137B.

*Length.*—3.2-4.5 cm.

*Width.*—2.3-3.5 cm.

*Shape.*—Ovate.

*Base shape.*—Attenuate.

*Apex shape.*—Acute.

*Margin.*—Palmately lobed; slightly dentate.

*Texture, upper surface.*—Heavily bifid T-shaped hairs.

*Texture, lower surface.*—Heavily bifid T-shaped hairs.

*Color of veins, upper surface.*—RHS 138B.

*Color of veins, lower surface.*—RHS 138B.

*Pattern of veining.*—Palmate.

*Petiole color.*—RHS 138B.

*Length.*—1.5-2.3 cm.

*Diameter.*—0.2 cm.

*Texture.*—Heavily bifid T-shaped hairs.

Stem:

*Quantity of main branches per plant.*—10-12.

*Color of stem.*—RHS 137C but appears much lighter grey due to the amount of hairs.

*Length of stem.*—15-19.0 cm.

*Diameter.*—0.4 cm.

*Length of internodes.*—0.5-1.0 cm.

*Texture.*—Heavily bifid T-shaped hairs.

*Color of peduncle.*—RHS 137C but appears greyer than stem due to the amount of hairs.

*Length of peduncle.*—6-10.0 cm.

*Peduncle diameter.*—0.175-0.2 cm.

*Texture.*—Heavily bifid T-shaped hairs.

Inflorescence:

*Type.*—Compositae, solitary decorative-type inflorescences borne terminally above foliage, ray florets arranged acropetally on a capitulum.

*Quantity of short days to flowering (response time).*—About 52 days.

*Natural season flowering.*—About mid-October.

*Quantity of inflorescences per plant.*—About 50 with about 100-125 buds at various stages.

*Lastingness of individual blooms on the plant.*—About 6 weeks from first color.

*Fragrance.*—Slightly spicy.

Bud (just when opening/showing color):

*Color.*—RHS 9A.

*Length.*—1.0-1.4 cm.

*Width.*—1.0-1.3 cm.

*Shape.*—Oblate.

Immature inflorescence:

*Diameter.*—3-3.5 cm.

*Color of ray florets, upper surface.*—RHS 9A.

*Color of ray florets, lower surface.*—RHS 6B.

Mature inflorescence:

*Diameter.*—4.7-5.3 cm.

*Depth.*—1.5 cm.

*Total diameter of disc.*—0.3-0.4 cm.

*Receptacle color.*—RHS 144B.

*Receptacle height.*—0.3-0.4 cm.

*Receptacle diameter.*—0.4 cm.

Ray florets:

*Average quantity of florets.*—About 170-180 in many whorls.

*Color of florets, upper surface.*—RHS 6A with slightly darker apex.

*Color of florets, lower surface.*—RHS 6B.

*Length.*—2.0-2.1 cm.

*Width.*—0.5 cm.

*Shape.*—Oblong.

*Apex shape.*—Retuse to slightly praemorse.

*Base shape.*—Cuneate.

*Margin.*—Entire.

*Texture, upper surface.*—Papillose.

*Texture, lower surface.*—Papillose.

Disc florets:

*Average quantity of florets.*—About 13-15.

*Color of florets.*—RHS 155C with RHS 17B apex.

*Length.*—0.4 cm.

*Width.*—0.1 cm.

*Shape.*—Tubular, elongated, with a flared apex.

*Apex shape.*—Acute, 5 pointed.

*Texture, inner surface.*—Glabrous.

*Texture, outer surface.*—Glabrous.

Phyllaries:

*Quantity.*—About 30, with distinct outer and inner types.

*Color, upper surface.*—Outer — RHS 137D; inner — RHS 137D.

*Color, lower surface.*—Outer — RHS 137A; inner — RHS 143B.

*Length.*—Outer — 0.6-0.9 cm; inner — 0.6-0.7 cm.

*Width.*—Outer — 0.2 cm; inner — 0.3 cm including papery edges.

*Shape.*—Lanceolate.

*Apex shape.*—Acute.

*Base.*—Fused.

*Margins.*—Entire; inner — also papery.

*Texture, upper surface.*—Glabrous.

*Texture, lower surface.*—Heavily bifid T-shaped hairs.

Reproductive organs:

*Pistil.*—1, found on both types of florets.

*Length.*—0.5 cm.

*Style color.*—RHS 1C but less green and more translucent.

*Style length.*—0.35-0.4 cm.

*Stigma color.*—RHS 2B.

*Stigma shape.*—Bi-parted and hairy or fuzzy on apex.

*Ovary color.*—Too immature at this stage.

*Stamens.*—4, found only on the disc florets.

*Color of filaments.*—RHS 1C but less green and more translucent.

*Length filaments.*—0.15 cm.

*Anther color.*—RHS 13B.

*Anther length.*—0.1 cm.

*Anther shape.*—Oblong.

*Color of pollen.*—RHS 14B.

*Pollen amount.*—Normal.

*Fertility/seed set.*—Has not been observed to date.

*Disease/pest resistance.*—Has not been observed to date.

What is claimed is:

1. A new and distinct variety of *Chrysanthemum* plant named 'CIFZ0009' substantially as illustrated and described herein.

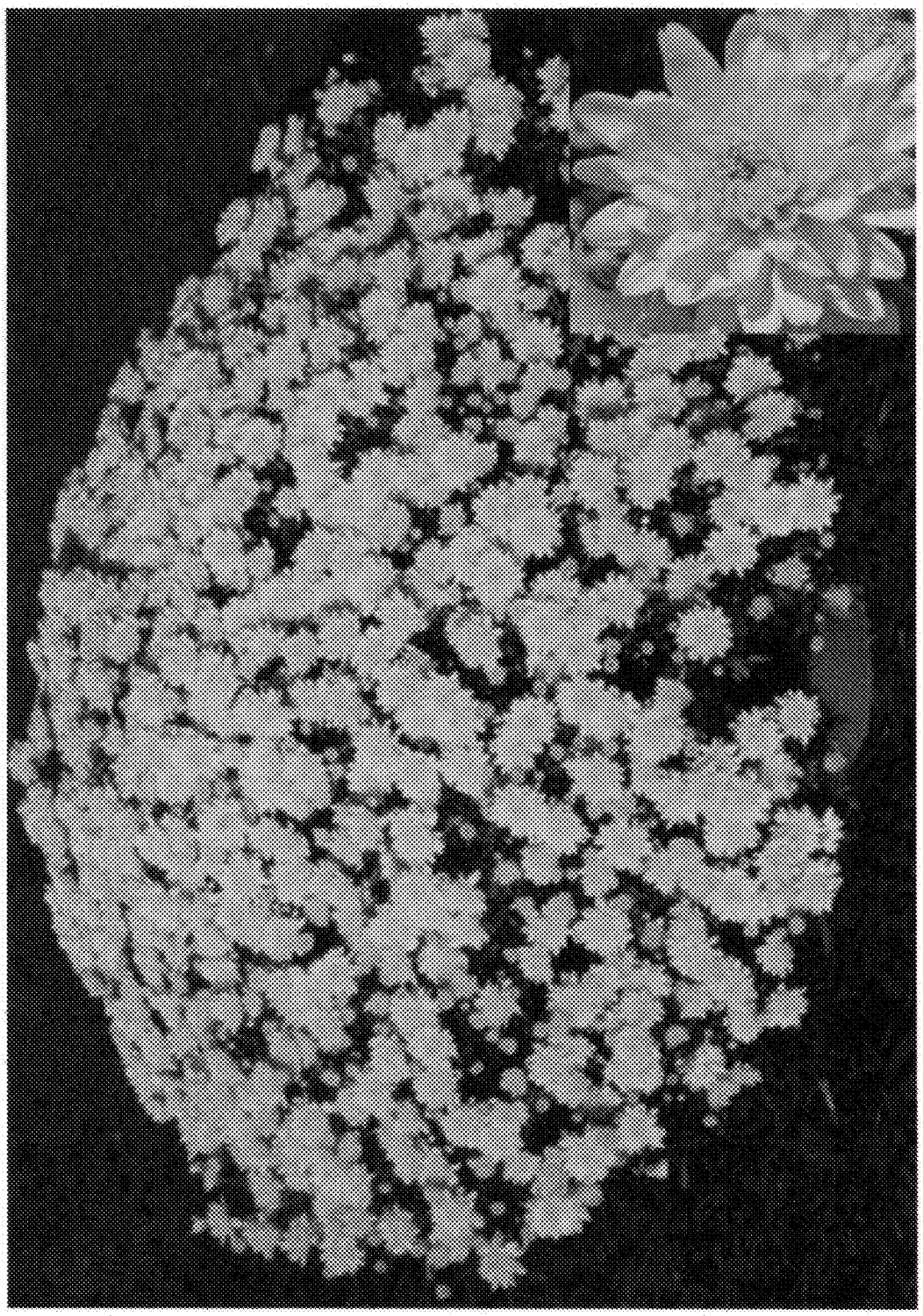

* * * * *